(12) United States Patent
Friebauer et al.

(10) Patent No.: US 11,918,428 B2
(45) Date of Patent: Mar. 5, 2024

(54) ORAL DEVICE, MANUFACTURING APPARATUS AND METHODS OF MAKING THE SAME

(71) Applicant: James R. Glidewell Dental Ceramics, Inc., Newport Beach, CA (US)

(72) Inventors: Wolfgang Friebauer, Costa Mesa, CA (US); Chunlin He, Irvine, CA (US); Christopher J. Kirkland, Tustin, CA (US); Robert Ryan Solorzano, Huntington Beach, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 17/644,402

(22) Filed: Dec. 15, 2021

(65) Prior Publication Data

US 2022/0104924 A1 Apr. 7, 2022

Related U.S. Application Data

(63) Continuation of application No. 16/353,242, filed on Mar. 14, 2019, now Pat. No. 11,224,500.

(60) Provisional application No. 62/642,778, filed on Mar. 14, 2018.

(51) Int. Cl.
*A61C 13/01* (2006.01)
*A61C 5/00* (2017.01)
*A61C 13/34* (2006.01)

(52) U.S. Cl.
CPC ............. *A61C 13/01* (2013.01); *A61C 5/007* (2013.01); *A61C 13/34* (2013.01); *A63B 2209/00* (2013.01)

(58) Field of Classification Search
CPC ................................. A61C 13/00–34
USPC .................................. 433/6, 168.1
See application file for complete search history.

(56) References Cited

U.S. PATENT DOCUMENTS

| | | | | |
|---|---|---|---|---|
| 3,905,106 A * | 9/1975 | Costa | ..................... | A61C 13/00 433/213 |
| 3,950,851 A * | 4/1976 | Bergersen | ................ | A61C 7/08 433/6 |
| 4,080,412 A * | 3/1978 | Colpitts | ................. | A61C 13/01 264/225 |
| 4,247,287 A * | 1/1981 | Gigante | ................. | A61C 13/00 433/199.1 |
| 4,248,807 A * | 2/1981 | Gigante | ................. | A61C 13/00 264/278 |
| 4,846,682 A * | 7/1989 | Ootsubo | ................ | A61C 13/18 433/167 |
| 5,103,838 A * | 4/1992 | Yousif | ..................... | A61F 5/566 128/859 |
| 5,304,062 A * | 4/1994 | Saitoh | ................ | A61C 13/0001 433/191 |
| 5,338,192 A * | 8/1994 | Weber | .................... | A61C 13/16 433/34 |

(Continued)

*Primary Examiner* — Matthew M Nelson
(74) *Attorney, Agent, or Firm* — Charles Fowler

(57) ABSTRACT

A custom oral device is provided that fits on the maxillary or mandibular arch of a wearer. The oral device comprises a tray that corresponds with the shape and size of a wearer's oral anatomy. A soft liner is disposed within an occlusal channel of the tray having an upper surface that comprises an impression having features that correspond to at least a portion of the wearer's dentition and in which the wearer's teeth align. An apparatus and a method for making the custom oral device are provided.

16 Claims, 9 Drawing Sheets

(56) References Cited

U.S. PATENT DOCUMENTS

| | | | | |
|---|---|---|---|---|
| 5,645,420 | A * | 7/1997 | Bergersen | A61C 7/08 433/6 |
| 5,672,305 | A * | 9/1997 | Kogure | A61C 13/20 264/102 |
| 8,567,408 | B2 * | 10/2013 | Roettger | A61C 5/90 128/861 |
| 8,607,798 | B2 | 12/2013 | Turkbas et al. | |
| 10,588,717 | B2 * | 3/2020 | Chun | A61C 7/20 |
| 2003/0186184 | A1 * | 10/2003 | Chishti | A61C 7/08 433/8 |
| 2006/0127859 | A1 * | 6/2006 | Wen | A61C 13/04 433/213 |
| 2007/0092853 | A1 * | 4/2007 | Liu | A61C 13/14 433/213 |
| 2009/0053669 | A1 * | 2/2009 | Liu | A61C 13/16 433/34 |
| 2010/0009308 | A1 * | 1/2010 | Wen | A61C 7/08 700/118 |
| 2013/0066236 | A1 | 3/2013 | Herman et al. | |
| 2013/0068237 | A1 | 3/2013 | Herman et al. | |
| 2013/0074851 | A1 * | 3/2013 | Herman | A63B 71/085 128/861 |
| 2013/0078594 | A1 * | 3/2013 | Leslie-Martin | A61C 7/08 427/2.29 |
| 2013/0081640 | A1 | 4/2013 | Herman et al. | |
| 2014/0238417 | A1 | 8/2014 | Turkbas | |
| 2014/0238418 | A1 * | 8/2014 | Turkbas | A61M 31/002 128/862 |
| 2014/0261465 | A1 * | 9/2014 | Turkbas | A63B 71/085 128/862 |
| 2016/0100917 | A1 * | 4/2016 | Howe | A61C 13/0004 264/16 |
| 2016/0157962 | A1 * | 6/2016 | Kim | B29C 65/48 156/242 |
| 2016/0158627 | A1 * | 6/2016 | Layzell | A61C 9/0006 264/16 |
| 2016/0263466 | A1 * | 9/2016 | Schwank | A63B 71/081 |
| 2017/0014212 | A1 * | 1/2017 | Fischer | A61C 13/081 |
| 2017/0055088 | A1 | 2/2017 | Rabel et al. | |
| 2017/0105817 | A1 * | 4/2017 | Chun | A61C 7/12 |
| 2019/0282345 | A1 * | 9/2019 | Friebauer | A61C 13/01 |
| 2020/0390594 | A1 * | 12/2020 | Yukita | C08L 23/12 |

* cited by examiner

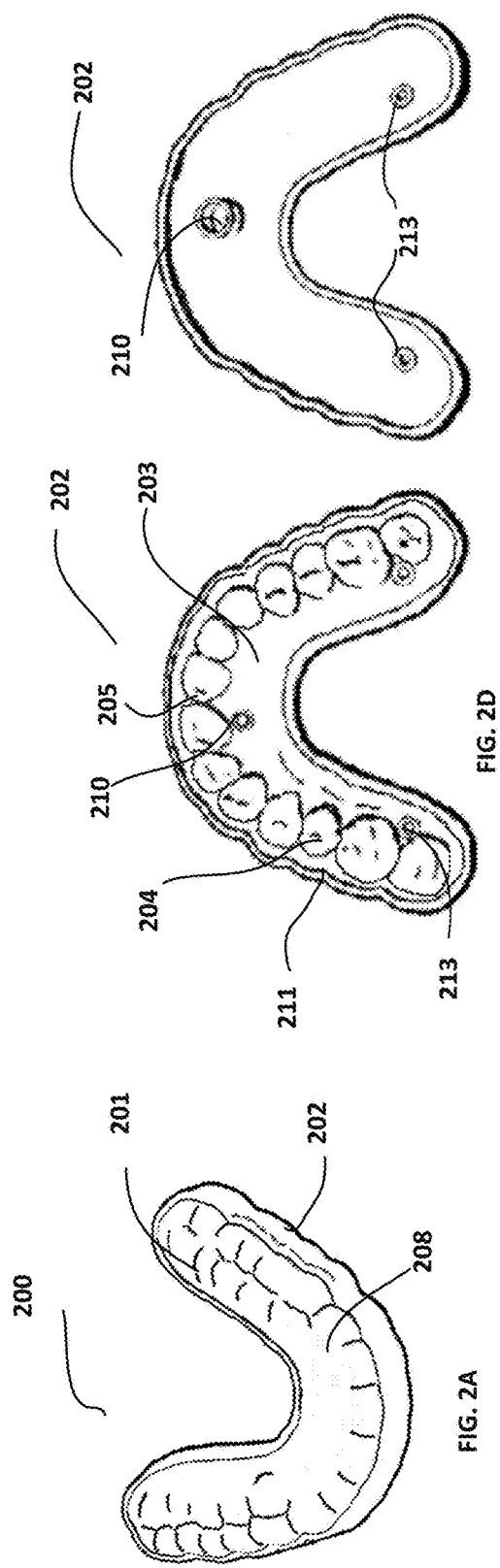
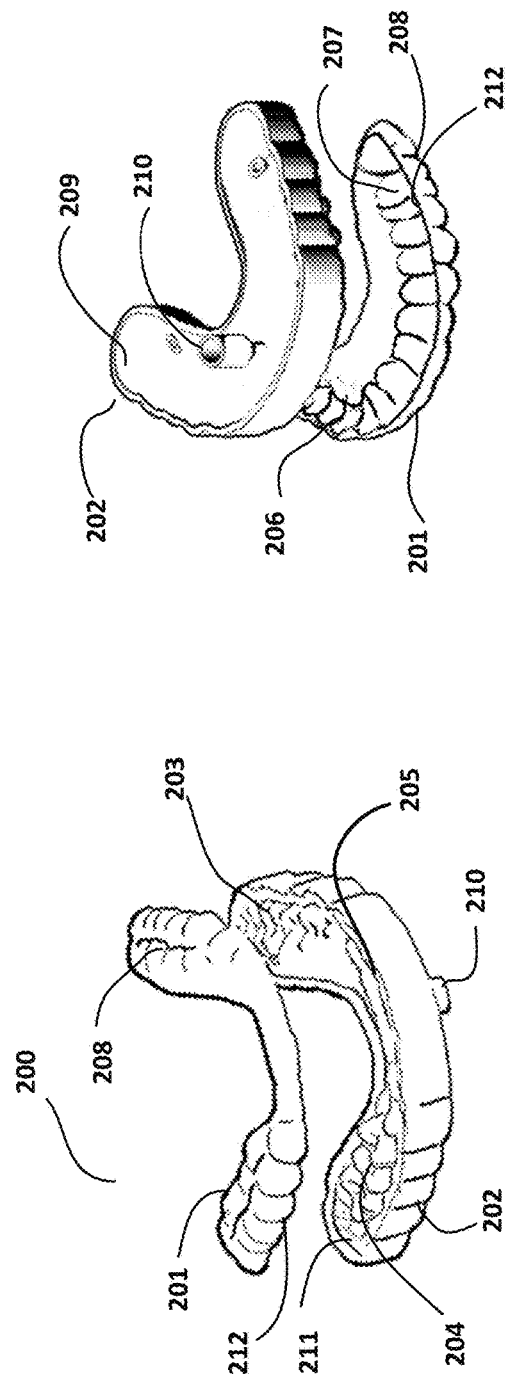

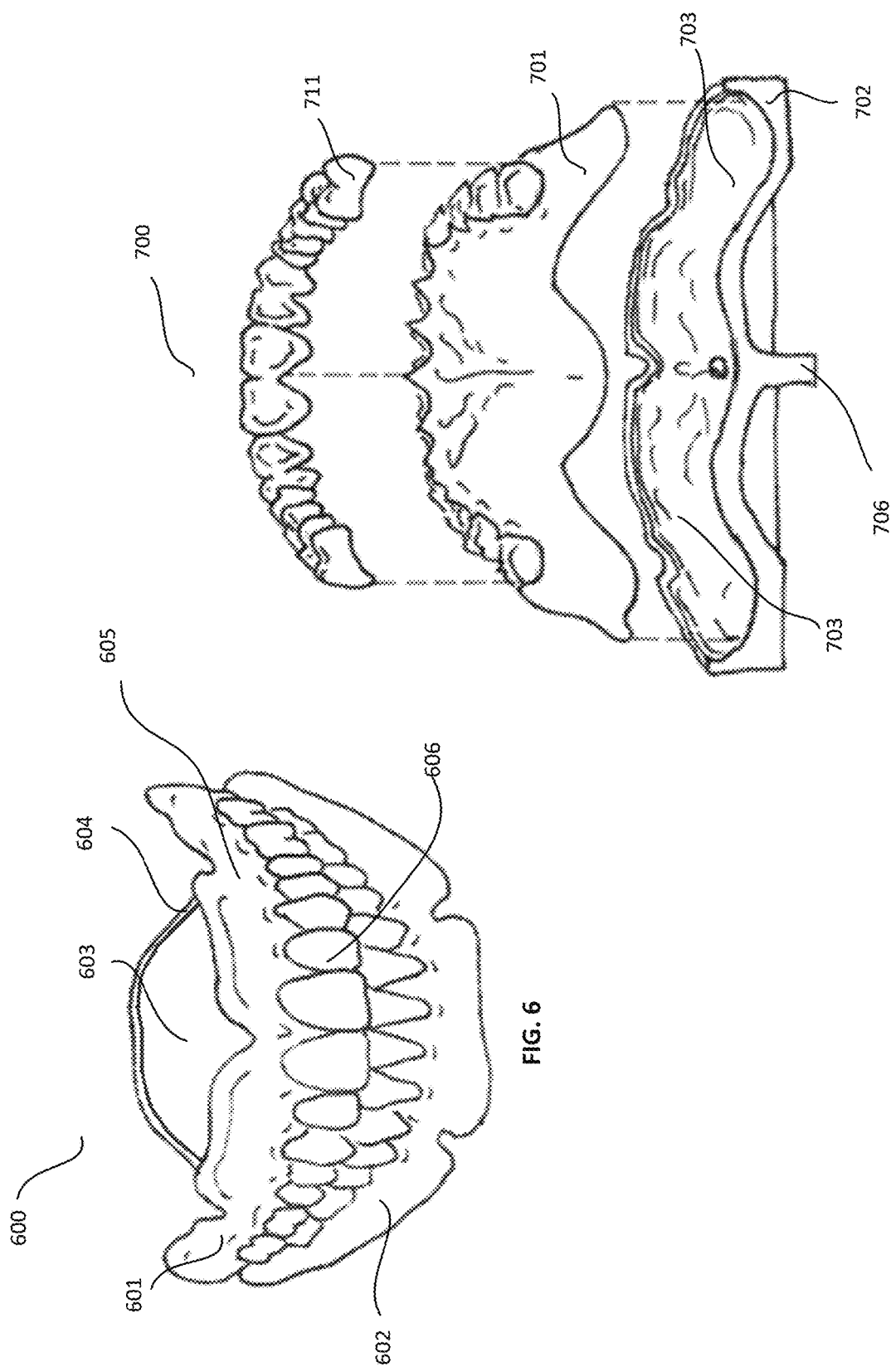

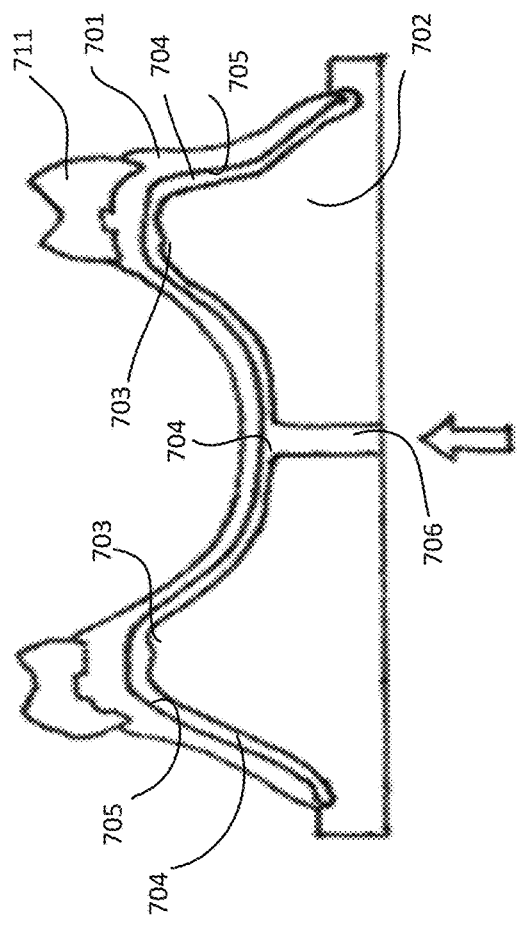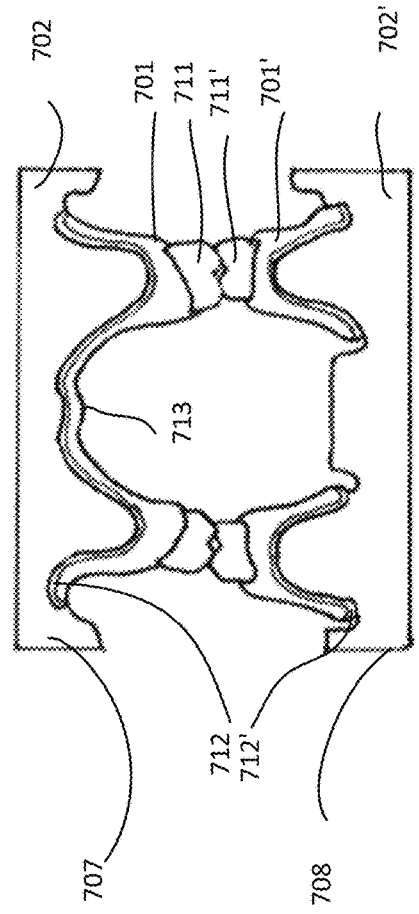

ORAL DEVICE, MANUFACTURING APPARATUS AND METHODS OF MAKING THE SAME

This patent application is a continuation of and claims the benefit of and priority to U.S. patent application Ser. No. 16/353,242, filed Mar. 14, 2019, which claims the benefit of and priority to U.S. Provisional Patent Application No. 62/642,778, filed Mar. 14, 2018, the entirety of each of which patent applications are incorporated herein by reference.

BACKGROUND

Oral devices or oral appliances are placed in the human mouth to treat orofacial disorders or protect the wearer's dentition from injury. Common examples of oral devices include dental splints for treating bruxism or for preventing oral injuries in sports, dental sleep devices for treating sleep apnea, and dental devices for replacing missing teeth, correcting tooth position or enhancing aesthetics.

Conventional methods for making custom-made oral devices include casting, thermoforming, or pressing a dental arch model from an impression or a 3D printed model of a person's dental arch, and then fabricating the device on the arch model.

SUMMARY OF THE INVENTION

Described herein are a method, a system and an apparatus for forming an oral device having a custom fit that conforms to a wearer's dentition. The oral device comprises a tray and soft liner that fit over a wearer's dental arch. The oral device comprises two or more materials bonded together, each component having distinct mechanical and/or chemical properties. A method for making the oral device may first comprise making an apparatus for forming the oral device.

A CAD (Computer-Aided Design) process that incorporates information specific to the wearer may be used to design the apparatus. The resulting design file may be used to make the apparatus by an automated, additive manufacturing process, such as 3D printing, or an automated subtractive process, such as milling, that replicates the wearer's features. The apparatus may be used in a molding process step, such as injection molding, to form the final dental device. Final dental devices may cover the incisal and/or occlusal surfaces, and optionally, at least a portion of buccal and/or lingual surfaces, of a wearer's dentition. The final dental device may be a dental splint that stabilizes or protects teeth, treats bruxism, facilitates proper occlusal positioning, or prevents oral injuries in sports, or a dental sleep device that treats sleep apnea, or a dental device that replaces missing teeth or corrects tooth position, such as a full-arch denture or a partial denture, including temporary and permanent removable dentures.

Exemplary 3D printing processes for making the apparatus include, but are not limited to 3D printing processes such as, fused deposition modeling (FDM), stereolithography (SLA) and selective laser sintering (SLS). In FDM technology, melted material is forced through a nozzle and deposited in single layers fused together to create a 3D object. A file (in e.g., .STL or .OBJ format) of the designed three-dimensional model of the apparatus may be imported into a program that slices the image into layers generating a g-code that is sent to the printer and controls the printer parameters. In SLA printing, a tank of liquid photopolymer or light-activated resin may be provided, and an object is formed on a platform as the resin is cured layer-by-layer upon exposure to a light source. SLA printing includes but is not limited to, laser-based printing and digital light projection-based printing. SLS printing processes include powder bed processes in which portions of a layer of powdered material on a build tray are sintered as a laser projects across the powder bed, and the tray is lowered to repeat the process forming another layer.

The apparatus may comprise a tray and a lid, either of which, or both, may be made by an additive or subtractive automated manufacturing process, such as 3D printing. The tray may comprise approximately a U-shaped cross-section that fits over the wearer's dentition, having first and second sides that taper to form an occlusal channel. When installed on the wearer's dental arch, the first side of the tray may cover all or a portion of the buccal surface of a wearer's dentition, the second side may cover all or a portion of the lingual surface of the wearer's dentition, and occlusal and/or incisal surfaces of the wearer's dentition fits within the occlusal channel.

The lid inner surface may comprise a structure that is a dental replica of at least a portion of the wearer's oral anatomy, similar to a physical or stone model made by a traditional impression technique. When assembled to form the apparatus, the structure comprising the dental replica located on a lid inner surface may be positioned within the occlusal channel of the tray. Characteristic features of the wearer's dentition and oral anatomy that may be replicated on the lid inner surface include, but are not limited to, dental arch size and shape, gingival features, tooth size and shape, position and orientation of teeth on the dental arch, teeth cusp and teeth groove features. For convenience, buccal surface and labial surface may be collectively referred to, herein, as facial surface, and incisal surface and occlusal surface may collectively be referred to herein as occlusal surface.

When assembled in a spaced arrangement, a cavity is formed between the inner surface of the occlusal channel of a tray and the dental replica on a lid. Within the cavity, a moldable material, such as a curable liquid, may be inserted, and upon curing forms a soft liner that may bond to the inner surface of the occlusal channel. The lid of the apparatus may be removed and discarded after the soft liner is formed.

In an embodiment, a final oral device comprises a tray on which a soft liner is disposed within the occlusal channel. After curing, the upper side of a soft liner comprises an impression of the replica of the wearer's dentition on the lid. The custom impression on the soft liner comprises recesses 109 having a custom fit to the dentition (e.g., the wearer's dental cusps) of a wearer, when installed in that wearer's mouth. The lower side of the soft liner, optionally, forms a bond with inner surface of the occlusal channel. Bonding between the tray and the moldable material may occur, for example, by self-curing, light, radiation or thermal processes. An optional finishing step, such as light polishing, may be performed on the outer surface of the tray to smooth the oral device.

Thus, in one embodiment, the oral device comprises a) a tray having an outer biting surface and an inner surface comprising an occlusal channel that fits the jaw of the wearer, wherein the occlusal channel optionally, has an impression comprising recesses that correspond to features of the wearer's dentition; and b) a soft liner within the occlusal channel having recesses on an upper surface in which at least a portion of the wearer's dentition fits, and that is optionally bonded to the inner surface of the tray.

Selection of materials from which to make the tray and soft liner may be based on desired performance properties. For example, the tray may be made from a material that is resistant to wear from bruxism, or having high flexural strength that resists breakage upon impact, or both. The inner liner, may comprise a soft material that conforms to the cusp of the wearer's dentition to provide comfort and/or protection from wear.

BRIEF DESCRIPTION OF THE DRAWINGS

FIG. 2a. An illustration of a top perspective view of a lid and tray assembled to form an apparatus according to one embodiment of the invention.

FIGS. 2b and 2c. Illustrations of opposing views of an apparatus comprising a tray and lid, in exploded form, according to one embodiment.

FIGS. 2d and 2e. Illustrations of the lid component of an apparatus from two opposing sides according to one embodiment of the invention.

FIG. 6. An illustration of an embodiment of an upper and lower denture device having a soft liner.

FIG. 7a. An illustration of an exploded view of components of an apparatus for forming a soft liner on a denture base.

FIG. 7b. An illustration of an apparatus for forming a soft liner on a denture base having denture teeth.

FIG. 7c. An illustration of an apparatus for forming a soft liner on an upper denture device and an apparatus for forming a soft liner on a lower denture device.

The invention may assume various alterative orientations, dimensions, designs or physical characteristics relating to the embodiments and step sequences, unless indicated otherwise.

DETAILED DESCRIPTION

Figure 1A:
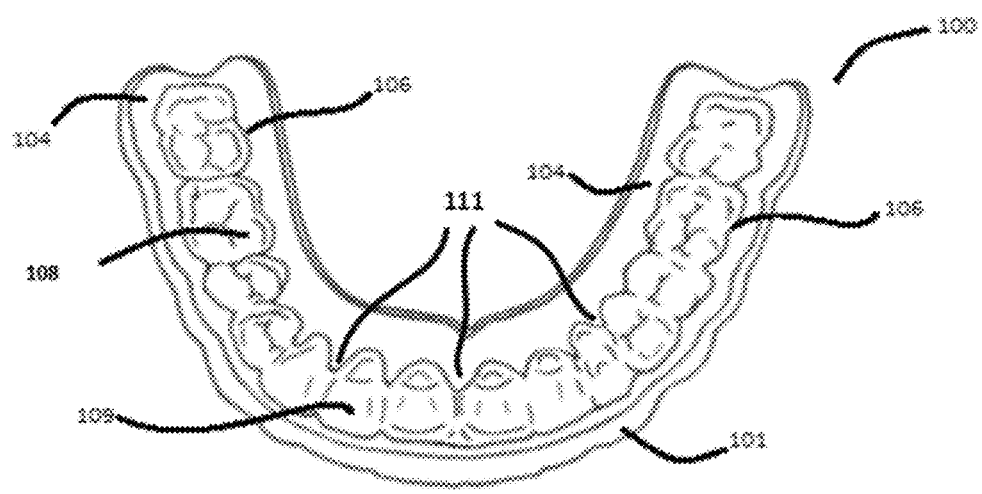
FIG. 1a. An illustration of a top down view of an oral device according to one embodiment of the invention.
Figure 1B:
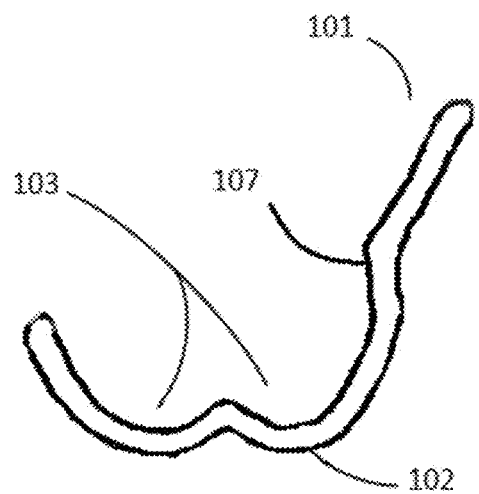
FIG. 1b. An illustration of a cross-sectional view of a tray component of an oral device without the soft liner.
Figure 1C:
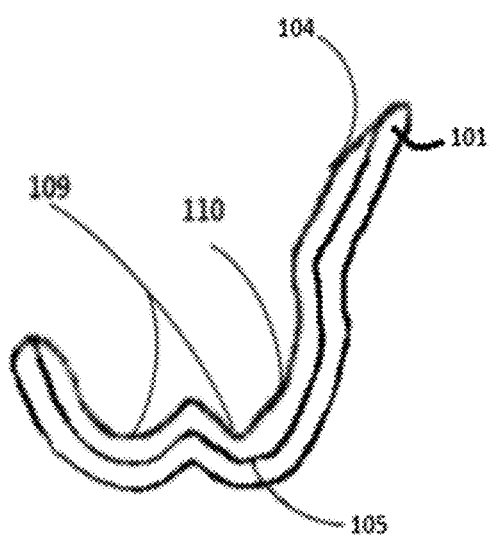
FIG. 1c. An illustration of a cross-sectional view of an oral device comprising a tray and a soft liner.

A custom oral device is exemplified in one embodiment in FIGS. 1a and 1c. In this embodiment, an oral device 100 is illustrated that fits over dentition on a maxillary or mandibular arch of a wearer. The oral device 100 comprises a tray 101 having a dental arch shape that corresponds with the shape and size of a wearer's oral anatomy. The tray 101, as illustrated in cross-section in FIG. 1b, has an occlusal channel 103 that fits over the occlusal/incisal surface of dentition. The tray 101 has an outer biting surface 102 opposite the occlusal channel 103; the outer biting surface of the tray may contact an opposing jaw when installed in the mouth of the wearer. A soft liner 104 is disposed within an occlusal channel of the tray 101 and has a lower surface 105, optionally, bonded to an inner surface 107 of tray within the occlusal channel 103. An upper surface 110 of the soft liner 104 comprises an impression 108 that correspond to at least a portion of the wearer's dentition, such as a contour or outline 106 of a coronal portion of dentition, recesses 109 in which the wearer's teeth cusps align when the device is installed on the wearer's dental arch and, optionally, gingival features, such as interproximal regions 111 between dental recesses.

In FIG. 2a, an exemplary apparatus 200 for making a custom oral device is illustrated comprising a tray 201 and lid 202, as assembled. FIGS. 2b and 2c illustrate an exploded view of the apparatus 200. The tray 201 and a lid 202 may approximate the size and shape of the wearer's dental arch, extending from a left side molar to a right side molar, as shown, or may cover only a portion of the dental arch. In one embodiment, the tray 201 of the apparatus becomes the tray 101 component of the final oral device 100. The tray 201 comprises an inner surface 206 and an occlusal channel 207 having a size and shape that fits over the wearer's dental arch and dentition. Oppositely, an outer biting surface 208 occludes with a biting surface of the wearer's opposing jaw, and the opposing jaw may comprise opposing natural or artificial dentition, or a second oral device installed on the opposing arch.

In one embodiment seen in FIGS. 2b and 2d, a lid 202 comprises a first side 203 having a geometry that replicates a portion of the wearer's anterior 205 and/or posterior 204 dentition, including incisal/occlusal portions of dentition and optionally surrounding gingiva. A second side 209 of the lid, optionally comprises one or more introduction ports 210, such as an injection ports comprising an opening that extends through the lid for use in an injection molding process. Optionally, one or more vent holes 213 form open passageways that extends through the lid from the first side 203 to the second side 209. When the apparatus 200 is assembled so that the lid encloses the inner surface of the tray and/or the occlusal channel 207, a cavity is formed in which the soft liner material is molded when forming the dental device. In the embodiment of FIG. 2a, an occlusal channel of the tray 201 is fully covered by the lid 202, when assembled. The lid may be discarded after formation of the final oral device 100, or saved to make a duplicate or replacement device.

Figure 3B:
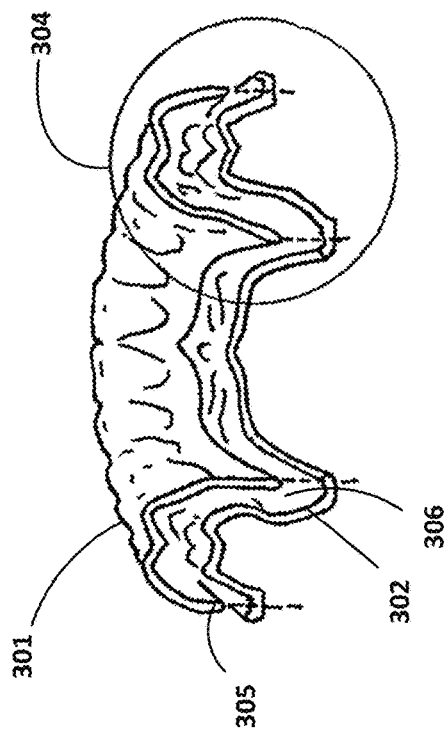
FIGS. 3a and 3b. Illustrations of an apparatus comprising a lid and tray, in exploded form, according to one embodiment of the invention.
Figure 3A:
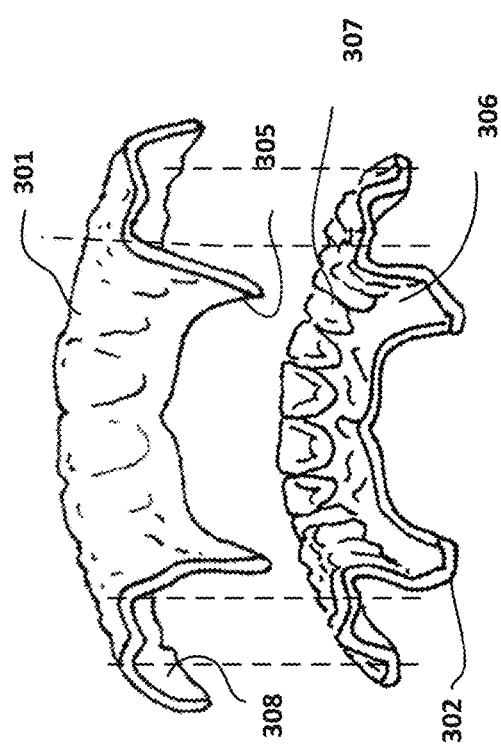
Figure 3D:
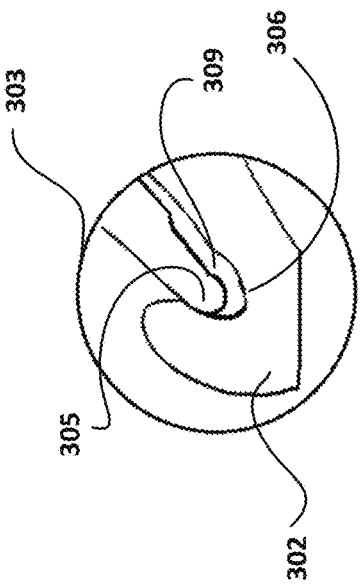
FIGS. 3c and 3d. Illustrations of enlarged cross-sectional views of a seal formed by the lid and the tray when assembled as the apparatus, according to one embodiment of the invention.
Figure 3C:
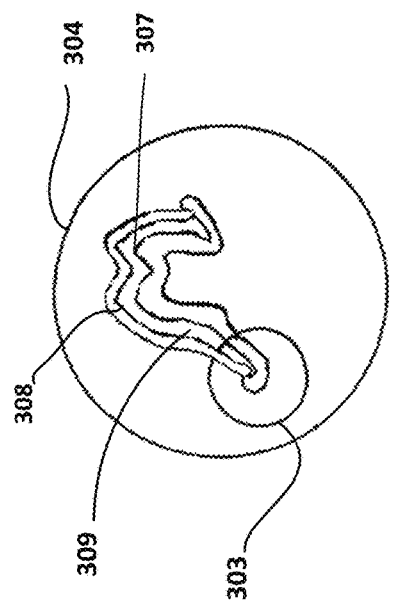

Optionally, the assembled apparatus comprises a seal, such as a press-fit or friction-fit seal, around the perimeter to enclose or seal off the occlusal channel when forming the soft liner. In one embodiment, a mechanical seal is formed which comprises a lip and/or groove 211 on the lid 202 and a complementary mating geometry, such as a rim 212, around the perimeter of the tray. In an exemplary embodiment, illustrated in exploded views in FIGS. 3a and 3b, and as assembled in FIGS. 3c and 3d, a tray 301 and lid 302 are assembled to form a press-fit seal 303. As seen in the assembled apparatus cross-section 304, a seal 303 is illustrated in FIG. 3c and as further enlarged, in FIG. 3d. When assembled, a rim 305 around the perimeter of the tray 301 fits within a groove 306 of the lid 302. Optionally, the seal may comprise a sealant material or chemical seal, such as a gasket, around the perimeter of the assembled apparatus to provide a liquid-resistant or waterproof seal. A volume of flowable or liquid curable material injected to form the soft liner may be held within the cavity 309 between the dental replica 307 and the occlusal channel 308 by the seal.

Figure 4B:
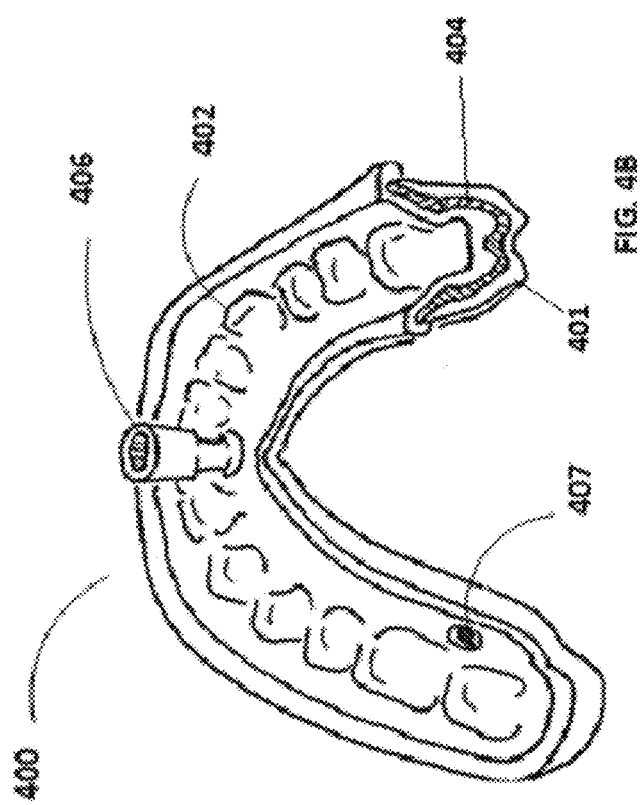
FIG. 4b. An illustration of an apparatus comprising an assembled lid and tray with soft liner material, according to one embodiment of the invention.
Figure 4A:
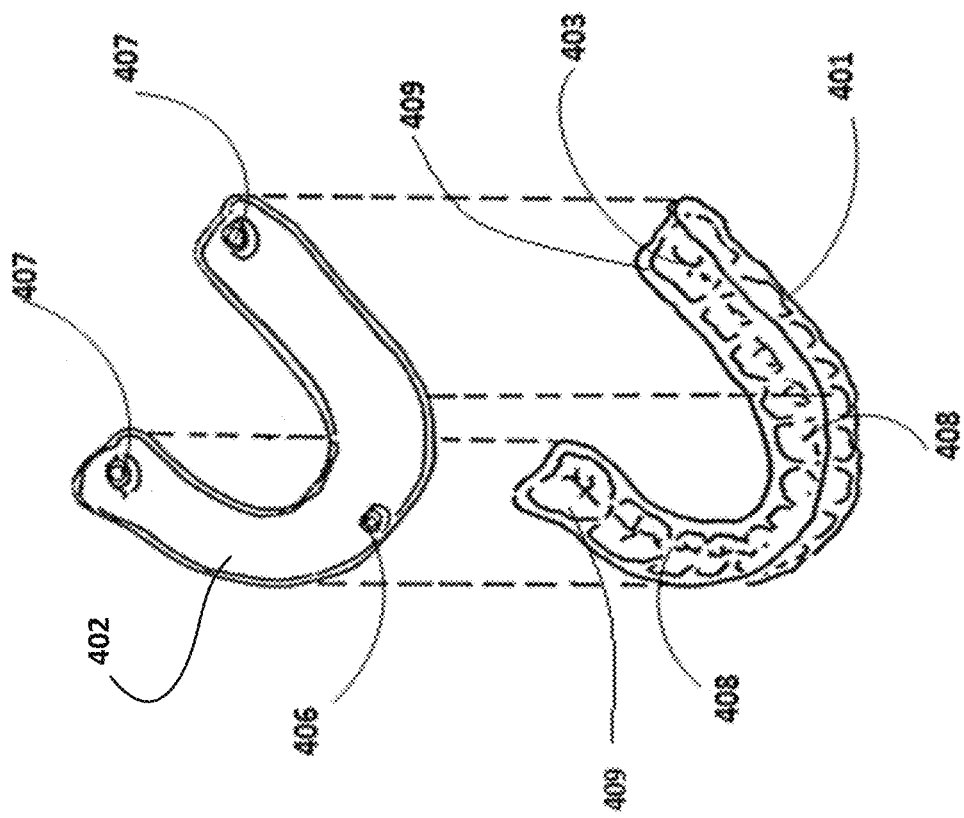
FIG. 4a. An illustration of an exploded view of an apparatus according to one embodiment of the invention.
Figure 4C:
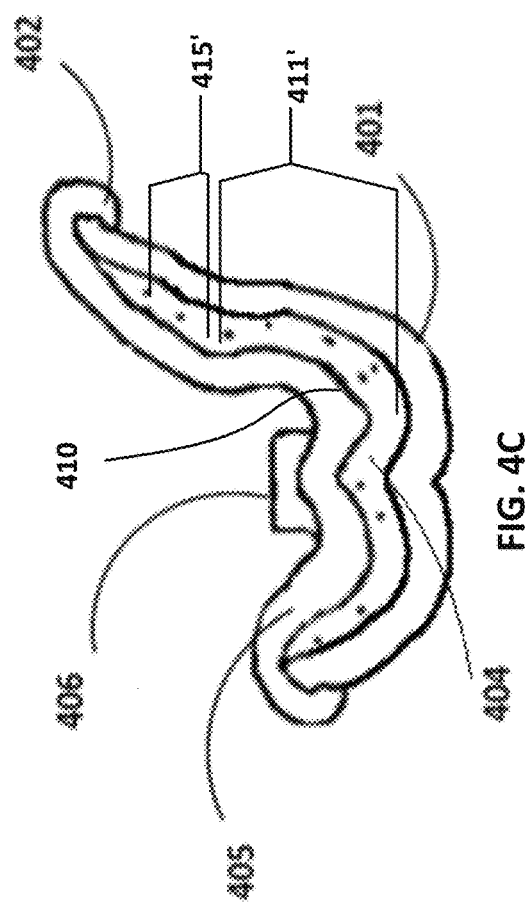
FIG. 4c. An illustration of a cross-sectional view of an apparatus comprising a soft liner material within a cavity, according to one embodiment of the invention.
Figure 4D:
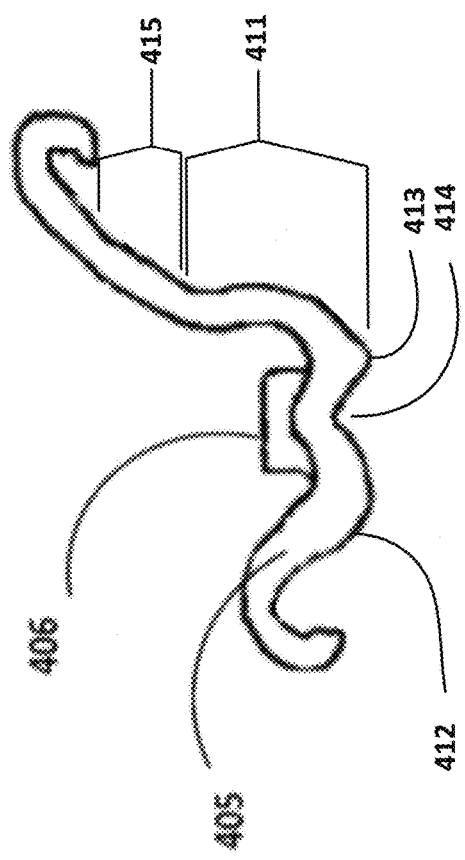
FIG. 4d. An illustration of a cross-sectional view of a lid portion of an apparatus, according to one embodiment of the invention.

As illustrated in FIGS. 4a-4d, an exemplary embodiment of the apparatus 400 comprises the tray 401 and lid 402 in exploded form (FIG. 4a) and, as assembled (FIGS. 4b, 4c). A lid 402 is shown having a size and shape that coincides with the general (arch) shape of the tray 401, and a cross-sectional view of the lid is illustrated in FIG. 4d. In accordance with this embodiment, a cavity is formed between the dental replica 405 of the lid and the occlusal channel 403 of the tray. A malleable or liquid curable material 404 may be introduced in the cavity to form the soft liner. The soft liner material conforms to the surface of the dental replica 405 of the lid 402, forming a negative model, or an impression, of the dental replica 405 on an upper side 410 of the soft liner. The dental replica comprising characteristic features of the wearer's oral anatomy may include a replica of the coronal region of anterior and/or posterior teeth 411, including a replica of teeth curves 412, ridges 413, grooves 414 and contours, and optionally, a gingival replica region 415 replicating gingival features.

In one embodiment, a curable liquid is introduced into the cavity through one or more openings in the assembled apparatus. One or more openings may include an injection (introduction) port 406, for example, in which a syringe may be inserted in an injection molding process to inject curable material for making the soft liner into the cavity. One or more vent hole 407 may be included for releasing gas or air while the curable soft liner material is being introduced into the assembly during a molding process. Curable material 404 contained within the cavity solidifies around the dental replica of the lid, and the final dental device 100 of FIG. 1A is formed that comprises the soft liner 104 disposed in the occlusal channel 103 of the tray 101. The upper side 110, 410 of the soft liner has an impression 108 of at least a portion of the dental replica on the first side of the lid 405, and may include an impression of biting surface (e.g., incisal, occlusal or both) features, contour features of a coronal portion of the wearer's dentition, dental ridges, cusps and grooves, and gingival features.

In one embodiment, the tray 401 also incorporates characteristic features of the wearer's dentition. For example, the occlusal channel 403 of the tray may comprise an occlusal impression 408 having recesses corresponding to facial and labial coronal contour features and/or occlusal surface features (for example, cusp, ridge, groove and/or edge features) approximating a negative or mold of the wearer's dentition. The occlusal impression 408 may comprise an outline 409 of the biting surface of the dental arch, interproximal regions, and/or contour of a coronal portion of all or some of the wearer's dentition. Curable material that is introduced in the cavity may fill the occlusal impression forming a soft liner having a relief on the lower surface of the soft liner that captures features of the impression in the tray. Thus, in one embodiment, the lower side 105 of the soft liner may have a relief replicating features of the occlusal impression that corresponds with the occlusal surface of the wearer's dentition, while the upper side of the soft liner 104 comprises an impression 108, or a negative, of the wearer's dentition from the dental replica.

Sharp characteristic features, such as occlusal surface ridges and grooves, may optionally be softened or eliminated on the replica of the lid, the impression of the tray or both. As used herein, the terms incisal and occlusal may be collectively referred to by the term occlusal, for example, where occlusal channel, occlusal surface or occlusal feature encompasses both anterior and posterior dental biting surface features, for convenience. The terms buccal and labial may be collectively referred, herein, by the term facial.

In one embodiment, contour dimensions of the occlusal impression of the tray are larger than the contour of the wearer's dentition replicated on the lid to provide a space between the tray and lid that forms the cavity. The overall size of the impression on the occlusal channel of the tray may be enlarged, for example, by a software program suitable for use in dental device design. In one embodiment, dimensions of an occlusal impression 408 of the tray are uniformly larger than the dimensions of corresponding features of the dental replica of the lid 405, and an enlargement dimension of the occlusal impression of the tray may be equivalent to the thickness of the soft liner provided therein.

When assembled as an apparatus, a vertical offset distance between the inner surface of the tray and the adjacent surface of the lid, optionally, may be uniform throughout the coronal region 411 replicated on the lid. For example, the offset distance is substantially the same adjacent an occlusal surface and a facial surface, and/or interproximal regions between. The material thickness of the resulting soft liner may be substantially the same at an incisal or occlusal edge and a groove or recess of an incisal/occlusal surface, or a buccal/lingual surface and an interproximal region (between adjacent teeth). The offset distance may be the same at an anterior tooth region, such as an incisor or cuspid, and a posterior tooth, such as a molar. An offset distance may be substantially uniform at a coronal region 411 and an adjacent gingival region 415, and the resulting soft liner comprises substantially uniform thickness where it contacts the coronal region 411' of a wearer's teeth and where it contacts a gingival region 415'.

In traditional thermoforming techniques, an oral device may lack predictable and/or uniform material thickness around the contour of a tooth. For example, a thermoformable plastic sheet material, stretched under heat, pressure and/or vacuum over a dental model may result in material thinning adjacent sharp or convex surfaces, such as, the ridges of an occlusal surface or incisal edge. A resultant material build-up may occur as thermoformable material fills concave surfaces or grooves, such as, interproximal spaces or occlusal grooves. By methods described herein, a soft liner may be formed having a thickness that is uniform at both convex surfaces and edges, and concave surface grooves, providing comfort, protection, stability and support by both the rigid tray material and the soft liner by the step of creating a uniform offset distance within the cavity.

In a further embodiment, a method and an apparatus for forming a soft liner on a fitting surface of a denture is provided. As exemplified in FIG. 6, a denture 600 may comprise an upper 601 denture and/or lower 602 denture that comprises a base 605 and denture teeth 606. A soft liner 603 is provided to a fitting surface 604 on the base of an upper denture 601 that abuts the soft palate or gum tissue of a wearer's upper jaw, or a fitting surface of a lower denture 602 that abuts the gum tissue of a lower jaw.

FIG. 7a comprises an illustration of an exploded view of components of one embodiment of an apparatus 700 for forming a soft liner 603 on an upper 601 or lower 602 denture. An apparatus comprises a denture base 701 (with or without denture teeth 711 attached) and a lid 702. The lid 702 comprises a replica of gingival structures 703 of a wearer, having a size and shape that aligns with the fitting surface 705 of the denture base 701 when assembled as shown in the cross-sectional view of FIG. 7b. A cavity 704 formed between the fitting surface 705 of the denture base 701 and replica of the gingival structure 703 of the lid 702 provides a space for the soft liner material. The height of the cavity 704 comprises a selected offset distance between the gingival structure 703 of the lid and the fitting surface 705 of the denture base. The lid 702 may comprise an injection port 706 for injecting material into the cavity 704 to form the soft liner, or the soft liner may be formed from material that has been pressed between the lid and base. Denture teeth 606, 711 may be secured to the denture base before, during or after the process of forming and bonding a soft liner to the fitting surface 604 of the denture base.

FIG. 7C is a cross-sectional illustration of an embodiment of an upper denture assembly 707 for forming a soft liner on an upper denture, and a lower denture assembly 708 for forming a soft liner on the lower denture. In this embodiment, each assembly comprises a lid 702, 702' that comprises a replica of the fitting surface of the wearer's edentulous jaw, a denture base 701, 701', and denture teeth 711, 711'. The soft liner 712, 712' formed from material that fills a cavity between the denture base and the lid when assembled, may be located on the fitting surface adjacent the gum tissue of the edentulous ridge of the wearer, and optionally, an upper denture may comprise soft liner 712 on a palatal region 713 of a fitting surface that abuts a portion of a palate of a wearer.

Figure 8A:
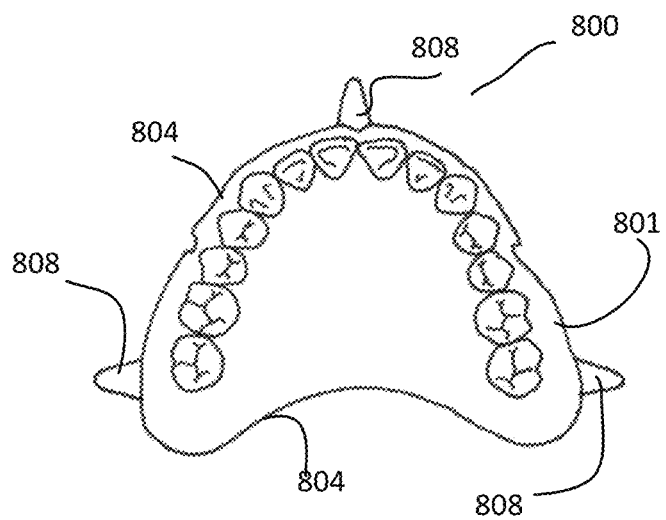
FIGS. 8a, 8b, and 8c. An illustration of an apparatus for forming a soft liner on a denture device.
Figure 8B:
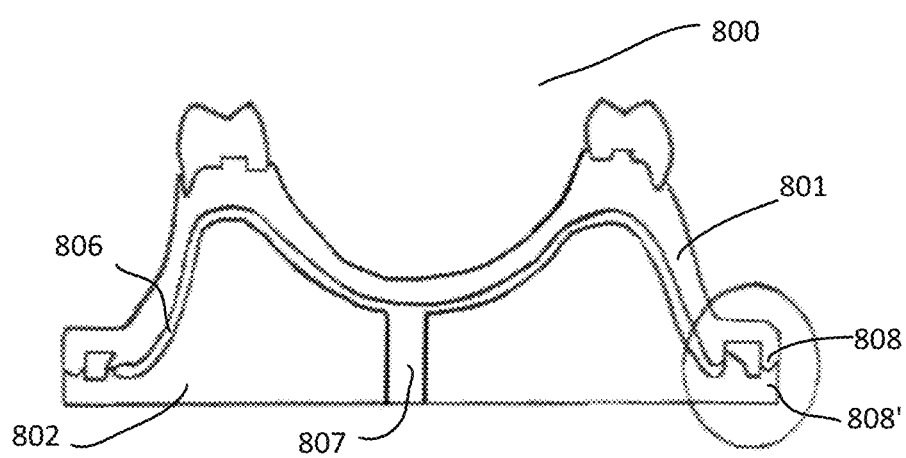
Figure 8C:
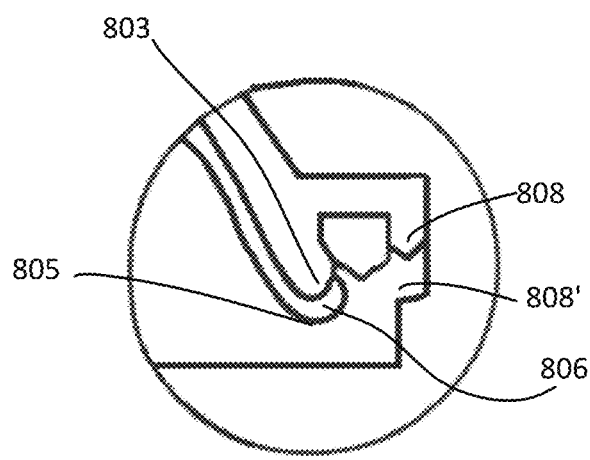

In a further embodiment exemplified in FIGS. 8a, 8b, and 8c, an apparatus 800 for forming a soft liner on a fitting surface of a denture is provided, wherein a denture base 801 and a lid 802 are fastened together for forming the soft liner. For example, the denture base 801 and lid 802 may be fastened together by clamping. Alternatively, the assembled apparatus 800 may comprise a seal such as a mechanical interference fit, friction fit or press fit fastening mechanism. In one embodiment, the perimeter 804 of the base 801 may comprise a lip, or edge, 803 that fits within a groove 805 around the perimeter of the lid 802 to form a seal. The press fit seal retains soft liner material within the cavity 806, for example, during an injection molding process. A curable liquid soft liner material may be introduced by a syringe through an injection port 807 that has an opening extending through the lid into the cavity.

Further, the assembly may comprise a mechanism for maintaining the vertical alignment between the denture base 801 and a lid 802 during an injection molding process. For example, the denture base 801 may have one or more alignment components, such as a guide, column, bolt or a pin 808, around the perimeter 804 of the base that aligns with one or more complementary components 808' for receiving the pin 808 on the lid 802. Pairs of complementary components may have mating geometries, and upon alignment of components 808 and 808', uniformity of cavity height during an injection molding process is maintained throughout the assembly. After formation of the soft liner on the fitting surface of the denture base, the alignment components may be removed from the base by hand or by milling, and the lid may be discarded.

In a further embodiment, the design of the cavity of the assembled apparatus may depend on the function of the final oral device. The dimensions of the cavity of the apparatus may be enlarged, decreased or eliminated in selected regions to increase or decrease soft liner thickness in designated areas. For example, one embodiment of an oral device that protects dentition from deterioration due to bruxism the thickness of the hard tray material is greater at posterior dental regions of the tray than at an anterior dental tray region. Nonetheless, the oral device may have a uniform combined thickness (soft liner and the tray) throughout the tray by proportionately increasing the height of the cavity in the anterior region, forming a proportionately thicker soft liner material in the anterior region of the final dental device. Alternatively, the cavity height and soft liner thickness are decreased or eliminated at posterior regions proportionately to the increased thickness in hard tray material; the resulting oral device has a uniform combined thickness in both anterior and posterior regions of the dental splint. Optionally, an apparatus may be selectively provided with a cavity in only a portion of the dental arch, such as, only a portion of the anterior or posterior regions. The resulting final oral device may have a soft liner covering in selected areas or on selected surfaces of the anterior and posterior regions of the occlusal channel of the tray.

The material of the tray and the lid may be selected based, in part, on the manufacturing process selected for each component. For example, when made by an additive manufacturing process such as SLA, the tray and/or lid may comprise the polymerization product of an acrylate monomer or methacrylate monomer, or a methacrylate oligomer or acrylate oligomer, or a combination thereof. The tray or lid may be comprised of a commercially available acrylic polymer, such as a copolymer of an acrylic ester and a methacrylic ester. For FDM or SLS processes, for example, the tray and/or lid may comprise a thermoplastic polymer, including, but not limited to acrylonitrile butadiene styrene (ABS), polylactic acid (PLA), high-impact polystyrene (HIPS), thermoplastic polyurethane (TPU), aliphatic polyamides (nylon), and polyether ether ketone (PEEK), or a combination of thereof.

The soft liner also may be derived from an acrylic acid or methacrylic acid, including, but are not limited to, the polymerization product of an acrylate monomer or methacrylate monomer, or a methacrylate or acrylate oligomer, or a combination thereof.

The tray may be comprised of a material that is more rigid or stiff than the soft liner, while optionally maintaining some flex for comfort, depending on the application of the final device. Tray material may have a greater modulus value compared to the soft liner, for example, when tested according to ASTM D638 (Young's Modulus). The tray may be comprised of material having greater hardness than the soft liner, for example, when measured according to ASTM D2240. In some embodiments, materials suitable for use as a tray material have a Shore D hardness value between 40 and 100, or between 50 and 100, when cured, and tested according to ASTM D2240 Shore Durometer, type D scale. In some embodiments, a suitable cured, soft liner material has a Shore A hardness value of between 10 and 90, or between 40 and 80, when cured, and when measured according to ASTM D2240 Shore Durometer, type A scale.

In traditional thermoforming processes, an oral device may be formed from a material comprised of two layers, such as a harder first polymer layer and a softer second polymer layer. The layers of the material may be bonded by the application of heat, in which the two polymers soften and flow, forming a blend of the two polymers that bonds the two polymer layers. In the methods provided herein, an indirect bond between the lower side of the soft liner and the inner surface of the tray may be formed by the addition of an adhesive between the tray and the soft liner. The adhesive may be applied as a liquid, powder, spray coating or adhesive material layer. In one embodiment, the adhesive is placed within the occlusal channel prior to introducing the curable, soft liner material. Once the soft liner material is formed within the apparatus, the adhesive bonds the soft liner to the tray.

In an alternative embodiment, a chemical bond is formed between the tray and the soft liner. The chemical bond may comprise the reaction product of an uncured portion of the tray material and reactive groups of the polymerizable soft liner material. In one embodiment, a tray is comprised of polymerized material having sufficient "green" strength to undergo further processing steps for incorporating a soft liner material, while having uncured tray portions that chemically bond with the soft liner material. For example, the tray inner and outer surfaces may be uncured, or, alternatively, the tray may comprise an uncured portion on only the tray's inner surface 206. Upon introduction of soft liner material into the cavity, reactive groups on the tray's inner surface may chemically bond with the lower side 105 of the soft liner upon polymerization of the soft liner material.

Chemical bonding may be achieved by a self-curing reaction between the tray and soft liner material, or upon the application of an external energy source such as a light or heat source, to initiate reaction between the reactive groups of the polymerizable soft liner material and tray inner surface material. In one embodiment, where chemical bonding of the soft liner and tray material utilizes an external light source, the tray material may be at least partially transparent to the light to facilitate curing of the inner surface of the occlusal channel.

In one embodiment, a tray comprises a first curable polymer material that is the same or different from the soft liner material. In one embodiment, the tray or soft liner may comprise a first polymerizable composition comprising,

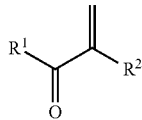

where R1 and R2, independently may be an aliphatic, aromatic or amine substitute. Optionally, the tray is comprised of a polymeric materials that is different than the soft liner, and the tray or soft liner comprises a second polymerizable composition that comprises a thiol group, a vinyl group, an alcohol group, a primary amine group or secondary amine group,

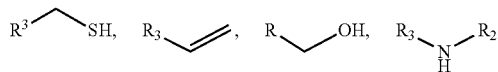

where R, R2 and R3, independently may be an aliphatic, aromatic or amine substitute. In one embodiment R2 is H, or an aliphatic, aromatic or amine substitute. Optionally, the second polymerizable material may comprise dimethyldichlorosilane,

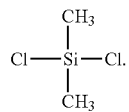

In one embodiment where at least one material comprises an acrylic acid, both the first and second polymeric materials may comprise a thiol group.

The tray, soft liner or both, may incorporate a bioactive material including but not limited to an acrylate derivative, methacrylate derivative, or a thiol derivative having a cation such as a positively charged amine group, an anion such a negatively charged acidic group, including sulfate, carboxylate, phosphate, and the like.

In one embodiment, to provide release between the soft liner and the lid, or to prevent the lid from bonding to the upper surface of the soft liner during the curing step, the lid may be fully cured to reduce chemically reactive groups prior to introducing the curable material used to form the soft liner. In another embodiment, a blocking material may be placed adjacent the lid to prevent bonding with the soft liner. Suitable blocking materials may include, but are not limited to, chemically inert solid wax, flowable wax, silicon oil, fluoropolymer, or inert block copolymers.

The dimensions of the tray and soft liner may be unique to the wearer, and the thickness of the soft liner within the occlusal channel may vary depending on the intended purpose of the oral device. In some embodiments, such as a night guard device that protects teeth from the effects of bruxism, the soft liner thickness may range from about 0.25 mm to 3 mm, 1 mm to 3 mm, or 0.5 mm to 1 mm. In some embodiments, the tray thickness may be about 0.5 mm to about 3 mm, or about 1 mm to 2 mm. The combined, overall oral device thickness may vary depending on application, and in some embodiments, the overall thickness of the oral device may be from about 0.75 mm to 6 mm, or from about 1.5 mm to 5 mm, or from about 2 mm to 4 mm.

The dental device may be custom made for the individual wearer by first capturing the size and shape of the dental arch and characteristic features of the wearer's dentition or edentulous jaw in a computer-generated model of the wearer's mandibular and/or maxillary arch, dentition, and optionally, soft tissue features. By incorporating custom features from the computer-generated model of the wearer's dentition into the final oral device, an accurate size and a secure fit is obtained. In a computer-implemented process, a 3-D digital model of the wearer's dental arch, dentition and, optionally, soft tissue features, may be created by gathering image data from scans. For example, scan data of the wearer's oral situation may be collected directly through intraoral scanning (e.g., using iTERO® by Align Technology Inc. or TRIOS® scanner by 3Shape), or indirectly, by scanning an impression or a stone model prepared from an impression (e.g., using a desktop scanner). The data may be collected, for example, in a .dcm format, or other known format, that can be converted, for example, into a .stl format to create a computer generated 3D representations of the wearer's dentition. A computing system and software may be provided to perform a computer-implemented method to assemble a plurality of image data, such as scans or electronic photos, merging the images through known registration processes and commercially available dental design software to form a three-dimensional model of the wearer's jaw.

Figure 5A:
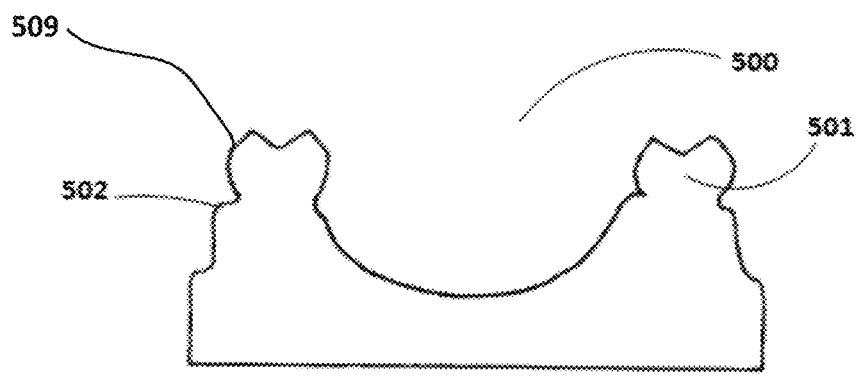
FIG. 5a. A cross-sectional illustration of a digital model of a wearer's oral anatomy.

A computer-implemented method is provided in which a 3D digital version of the apparatus comprising a lid and tray may be created based on the 3-D model of the wearer's dentition 500 using dental design software such as a 3 Shape Dental Designer™ program. In FIG. 5a, a virtual cross-section of a 3D model 500 of a wearer's jaw is provided replicating portions of a wearer's teeth 501 and gingiva 502. As illustrated from the buccal view of FIG. 5b, in a computer-implemented method a digital tray model 503 may be formed as an electronic impression of the 3-D model 500 of the wearer's digital mandibular or maxillary arch. A digital tray model 503 may comprise a digital occlusal channel corresponding to the shape of the arch and, and optionally, forms a depression capturing characteristic features of the wearer's teeth, such as grooves, ridges, facial surface features, edges, and/or, optionally, including soft tissue features, such as gingival and palatal features. The outer surface of the tray, opposite the occlusal channel, comprises the occlusal surface 504 that may replicate features of the biting surface of the wearer's dentition.

Figure 5B:
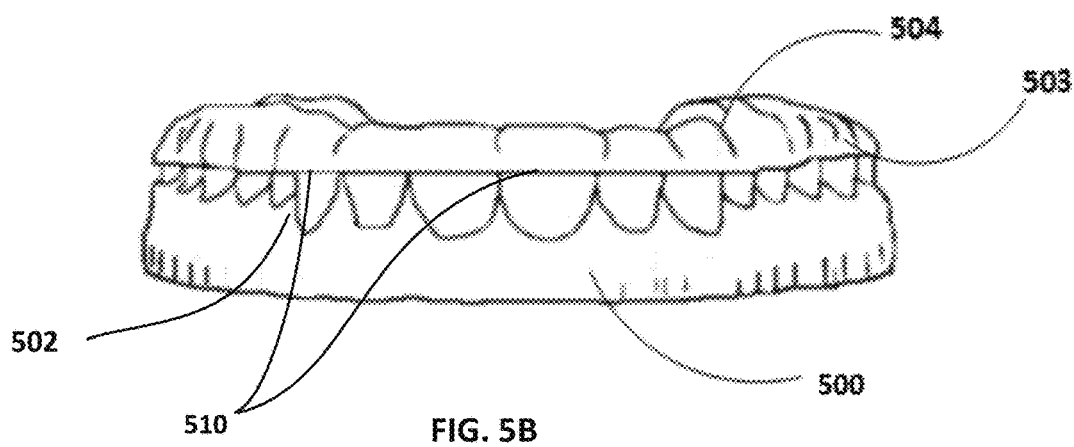
FIG. 5b. An illustration of a method step of forming a digital dental splint on a digital model of a wearer's oral anatomy.

The rim 510 of the digital tray model may extend beyond the incisal/occlusal surface 504 toward the gingiva 502, covering all or only a portion of the buccal 511 or lingual 512 surfaces of the dentition of the model 500. In the embodiment of FIG. 5b, the tray 504 covers all of the occlusal, incisal and lingual 512 surfaces of the teeth, and approximately one third to one-half of the visible buccal surface of the coronal portion of the teeth to protect teeth from bruxism. A portion of the buccal 511 surface teeth and gingiva is exposed for comfort. In another embodiment, the tray covers an occlusal/incisal surface and approximately the lower two thirds of the visible surface of the tooth when measured from incisal edge to margin or gingival sulcus. Optionally, the tray includes soft tissue features 505 of the gingiva and/or palate, as seen from the lingual view of FIG. 5c. In further embodiment, for example, wherein the final dental device is used as a sports mouth guard, the tray may entirely cover visible occlusal/incisal, buccal and lingual surfaces of the teeth, as well as at least a portion of the wearer's gingiva, to provide protection from impact.

Figure 5C:
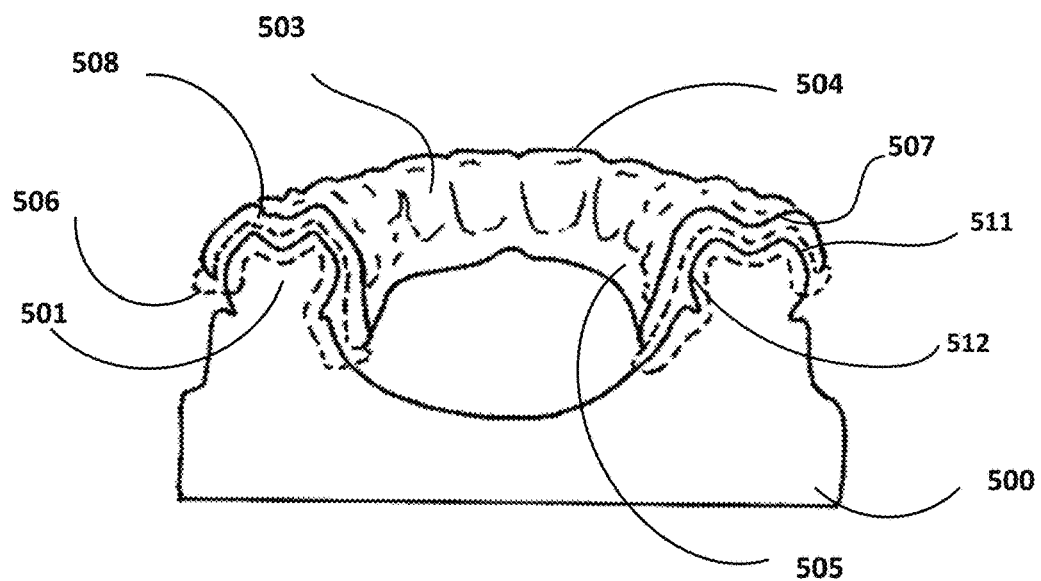
FIG. 5c. An illustration of a digital lid (illustrated in broken line), a digital tray, and a digital model of the wearer's oral anatomy.

A computer-implemented method comprises designing a digital lid model 506 for an oral device, as illustrated by the dashed lines 506 in FIG. 5c. In this embodiment, the digital lid model is designed between the surface of the digital model 500 of the wearer and the inner surface 507 of the digital model of the tray 503. The digital lid model may comprise a design that duplicates the size and shape of a portion of the model of the wearer's dentition 501 situated around the arch, optionally comprising characteristic features of the wearer's teeth, such as cusps, grooves, ridges, facial surface features, edges, and/or, optionally, including soft tissue features, such as gingival and palatal features.

In one embodiment, the inner surface 507 of the digital tray model may be digitally reduced by a specified value creating a uniform offset distance 508 between the dental replica surface on the lid and reduced inner surface of the tray when assembled. For example, the surface of the occlusal impression of the tray, which may include, for example, an impression of occlusal grooves, occlusal ridges, buccal/labial and/or lingual dental contours, may be uniformly reduced by a selected height, for example, in the range of 1 mm to 3 mm. Thus, a cavity may be formed between the reduced surface of the occlusal surface of the tray and the corresponding surfaces of the dentition 509 reproduced on the dental replica of the lid 506 when physical components made from the designs are assembled. In one embodiment, the occlusal impression of the tray model has a uniform surface height reduction of about 1 mm to 3 mm forming a distance between the lid and tray of about 1 mm to 3 mm, and a cavity height of about 1 mm to 3 mm. Advantageously, in this exemplary embodiment, the soft liner formed in the cavity has a corresponding uniform thickness between upper and lower surfaces (in this example, of about 1 mm to 3 mm) when measured at multiple locations such as an occlusal surface of a recess, a dental ridge, an incisal edge, a facial surface, and material that forms between recesses (e.g., interproximal region).

In one embodiment, a digital seal is designed between the lid and tray which when replicated in a physical apparatus will prevent leakage of a low viscosity curable material introduced within the cavity of the actual assembly during an injection molding process. Openings designed through the thickness of the digital tray or lid model form one or more ports for introduction of a curable liquid soft liner material, and optionally, vent holes for releasing air as the cavity fills with curable liquid material.

The digital design of the lid and tray may be provided by design software as one computer file, or two separate computer files, and stored, for example, in a computer memory. The files may be transferred to or accessed by an automated manufacturing machine through a direct connection to the computer system, or indirectly, for examples, by connection to a remote computer for example, by a network interface that receives or accesses the data files.

Automated manufacturing processes include, but are not limited to, additive processes generally referred to as 3D printing, or subtractive processes, such as CNC milling. 3D printing systems capable of converting the digital designs of the tray and lid into physical components include but are not limited to stereolithography, digital light processing, fused deposition modeling, selective laser sintering, selective laser melting, electron beam melting, and laminated object manufacturing. Examples of suitable 3D printing devices include those manufactured by 3D systems (Valencia CA) and Stratasys (Minneapolis, MN).

In one method, steps comprise i. forming the lid and the tray by a 3D printing process, wherein the material composition of the inner surface of the tray is not fully cured and comprises reactive groups; ii. assembling the tray and the lid by aligning the replica of the wearer's dentition on the lid within the occlusal channel of the tray to form an apparatus comprising a cavity; iii. injecting a liquid curable material through an injection port into the cavity; and iv. curing the liquid material to form a solid soft liner, wherein the reactive groups of the tray material chemically bond with the soft liner curable material, forming a direct bond between the soft liner and the tray together.

In another embodiment, a method comprises i. obtaining a tray having an inner surface and an occlusal channel and obtaining a lid having a dental replica of at least a portion of the wearer's dentition; ii. aligning the dental replica of the lid within the occlusal channel of the tray to form a cavity between the dental replica and the occlusal channel of the tray; iii. providing a curable material adjacent the occlusal channel; and iv. curing the curable material to form an oral device having soft liner with a lower surface bonded to the inner surface of the tray and an upper surface having an impression of the dental replica within which at least a portion of the dentition of the wearer fits.

In a further embodiment, a method is provided for forming an apparatus for making the custom oral device, that comprises, i. by a computer-implemented method utilizing a CAD process, designing a lid that comprises a dental replica of at least a portion of the wearer's dentition and a tray that comprises an inner surface, an occlusal channel and an occlusal impression of the wearer's dentition, ii. forming the lid and the tray by an automated manufacturing process using a polymeric material based on the design; iii. assembling the lid and the tray in a spaced arrangement to form an injection cavity between the dental replica and the occlusal impression, optionally, having a uniform cavity height; and iv. introducing a curable material into the injection cavity. The method further comprises curing the curable material, for example, by a light-curing process, forming a soft liner and chemically bonding the first surface of the soft liner to the inner surface of the tray during the curing step.

Optionally, the soft liner comprises features of the wearer's dentition on an upper surface of the soft liner, formed as an impression of the dental replica, comprising recesses within a portion of the dentition of the wearer fits. Optionally, the soft liner has a substantially, uniform thickness, for example, when measured at an occlusal surface of a recess and a gingival area between recesses, such as an interproximal region. In a further embodiment, the assembled apparatus comprises a seal wherein a lid has groove to accommodate the rim of a tray, and an injection port. Optionally, the occlusal channel of the tray comprises an impression corresponding to a portion of the wearer's dentition, and a lower surface of the soft liner formed therein has a negative impression of the occlusal/incisal surfaces of the wearer's dentition.

In another embodiment, an intermediate custom oral device comprises a tray having an uncured polymer material with reactive groups on the surface of an occlusal channel, and a lid having a dental replica that aligns within the occlusal channel when assembled. In another embodiment, an intermediate custom oral device comprises a tray having an uncured polymer material with reactive groups on the surface of an occlusal channel, and a polymerizable soft liner material disposed within the occlusal channel adjacent the reactive groups.

Examples of oral devices which may be made from the apparatus include, but are not limited to, dental splints for treating bruxism or for preventing oral injuries in sports, dental sleep devices for treating sleep apnea, and dental devices for replacing missing teeth or correcting tooth position. The oral device may cover a portion of the upper jaw of a wearer, the lower jaw of the wearer, or both the upper and lower jaw. An oral device may extend for the length of the entire jaw or only a portion of the jaw, such as, an oral device that covers one or more posterior portions or anterior portions. Advantageously, compared with conventional oral device and/or mouth guard fabrication methods such as casting, thermoforming or pressing, the method disclosed may have fewer manufacturing steps or have better fit by incorporating features of a wearer's dentition.

In a further embodiment, the oral device comprises a full or partial denture comprising a liner bonded to a fitting surface of the denture base, opposite the denture teeth. The liner may comprise characteristic features of the dental arch that are unique to the wearer to improve the fit and comfort of the denture device. In one embodiment, the liner covers all, or a portion of the fitting surface of the denture base. A method for making an apparatus for forming a liner on the fitting surface of a denture comprises, i. using a computer-implemented method, designing a lid that comprise a replica of a portion of the edentulous arch of the wearer, wherein the lid fits over the fitting surface of the denture base when assembled; ii. designing an offset distance between the replica on the lid and the fitting surface of the denture base, to form a cavity when assembled; and iii. using an automated manufacturing process to form a physical model of the lid based on the lid design.

A method of making a denture having a soft liner, comprises, i. obtaining a lid that comprises a replica of a fitting surface on the wearer's edentulous arch, and obtaining a denture base; ii. aligning the replica of the edentulous arch on the lid adjacent the fitting surface of the denture base, or within an channel of the denture base, to form a cavity; and iii. dispensing a curable material within the cavity and curing the curable material to form a liner. The liner may comprise a lower surface chemically bonded to the fitting surface of the denture base, and an upper surface having an impression of the replica of the edentulous arch. The liner may comprise the same materials described above for a forming the soft liner of a dental splint.

The denture base may be designed by well-known denture design and manufacturing techniques, such as CAD processes. The denture base may comprise a polymeric material known in the field of denture manufacturing techniques, including traditional denture casting processes, such as, polymers made from acrylate and/or methacrylate monomers, or derivatives thereof. In one embodiment, a denture base formed by an additive manufacturing process, such as three-dimensional printing process, comprises an uncured polymeric material having reactive groups on all or a portion of the denture base, including the fitting surface of the denture base. Optionally, reactive groups form a chemical bond with the polymerizable soft liner material upon reacting with the soft liner material, for example, the application of an external light source, where the polymeric materials comprise a photoinitiator system. In one embodiment, a denture teeth set may be aligned on the upper surface of a denture base that comprises reactive groups, and the denture teeth set may be adhered to a denture base upon curing the polymeric denture base material.

EXAMPLES

Example 1

An apparatus for making the oral device comprising a tray and a lid, was made that comprised information specific to the wearer's oral anatomy.

A digital splint, corresponding to the tray of the physical assembly, and a digital arch, corresponding to the lid of the apparatus, were designed as follows. 3 Shape design software was used to design the splint based on a digital model of the wearer's dentition. The digital model was formed from registration of scans obtained of a physical/stone model of the wearer's dentition. The digital splint was fitted to the digital 3D model of the wearer's dentition in 3 Shape design software and was conformed to the incisal/occlusal surfaces and at least a portion of the facial and lingual dental surfaces of the wearer model. Undercuts were removed around the perimeter of the splint, and the outer biting surface of the splint which comprised a relief of characteristic occlusal and contour dental features, was smoothed to remove rough edges and deep grooves. An inner surface of the splint, opposite the outer biting surface, that was conformed to the model of the wearer's dentition comprised an impression corresponded to the characteristic features of the wearer's dentition.

To form the lid, measurements were made of the size of the wearer's dental arch including total arch length, distance between rear molars, and height/width of teeth. A generic, solid body digital arch shape was created in Autodesk 123D Design software. The digital arch had a shape and dimensions slightly greater than the overall size of the wearer's arch including the dentition and a portion of the gingiva surrounding the dentition.

The arch shape was loaded and aligned with the digital 3D model of the wearer's dental arch in Autodesk Meshmixer. The arch was centered, and lowered until teeth and tissue made contact with arch surface, providing a replica with full anatomy on the arch. The arch was extracted from the model leaving a positive model of the wearer's dentition and a portion of the gingiva from the splint on a surface of the arch.

To form a cavity between the impression on the inner surface of the splint and the dental model on the arch, the impression on the splint and a portion of the gingiva were digitally reduced in Meshmixer. When assembled, the reduced inner surface of the splint and the dental model of the arch formed a cavity which, in when printed to form a physical apparatus accommodated curable material from a molding process that produced the desired thickness of curable material (between 1 mm and 1.5 mm).

To create an interlocking lid and tray in a physical apparatus, a portion of the perimeter of the arch around the dentition was reduced, forming a groove for a conformable fit between the lid and the rim of a corresponding tray when assembled. The outer perimeter of the splint had a rim or lip that fit within the groove of the arch when assembled.

An injection port was designed having a funnel in 123D Design software, and aligned with the arch in a location that provided ideal flow of injection material into the cavity and which provided minimal distortion of the teeth in Meshmixer. The shape of the injection port was removed from the arch design and the floating mesh left inside the injection tube was deleted creating a hollow section through the thickness of the arch. The injection port was merged with the arch over the port hole forming a conduit through the thickness of the arch design. Vent holes were formed through the thickness of the arch using a similar technique.

The digital file of the splint and arch with injection port were provided to a 3D printer to form the tray and lid, respectively. A 3D printer (Octave Light™, Octave Systems, Inc.) was equipped with a photopolymer to print the splint design forming the tray having a uniform final thickness of approximately 1.5 mm on side and bottom surfaces. The polymeric material was fully cured on the outer, occlusal surface of the tray, and a portion of the polymer forming the inner surface of the tray comprised residual uncured reactive groups. The arch design was printed to form the lid using the same 3D printer and polymer material, and was fully cured on all surfaces.

Example 2

An oral device for protecting teeth from grinding was prepared that comprised a tray and a soft liner material bonded directly to the tray without an intervening adhesive.

A tray and a lid made substantially according to Example 1 were obtained and assembled to form an apparatus. The tray comprised a perimeter edge that was press fit into a perimeter groove on the lid that surrounded the dentition forming a seal. The assembled apparatus comprised a cavity between the inner occlusal surface of the tray and the surface of the dental replica (of the wearer's dentition) on the lid that fit within the occlusal channel. The inner surface of the tray adjacent the cavity was not fully cured.

To form the soft liner, a liquid curable material capable of reacting with the uncured polymer of Example 1 was injected into the cavity through injection port 210 located on the lid. The uncured portion of the tray material and the injected liquid curable liquid were cured by the application of a light source. Upon curing, the injected liquid curable material formed a soft liner within the occlusal channel of the tray, and reacted with uncured tray material to form a direct bond with the inner surface 107 of the occlusal channel 103 of the tray. The lid was removed revealing an impression in the upper surface of the soft liner that corresponded to occlusal surface of the dentition of the replica from the lid.

The tray had a thickness of approximately 1.5 mm and a Shore D hardness of about 87. The soft liner had a thickness of approximately 1.5 mm when measured at impression recesses corresponding to the biting surface of dentition, interproximal regions, and gingival palatal regions, and the material had a Shore A hardness of about 64. The final oral device had a total thickness of approximately 3 mm. The liner had an impression having recesses that corresponded to characteristic features of the dental cusps of the wearer's dentition.

We claim:

1. An apparatus for making a denture device that fits over a wearer's upper or lower jaw, comprising:
    a. a denture base comprised of a polymeric material that fits over at least a portion of an edentulous ridge of the wearer's upper or lower jaw comprising
        a denture base outer surface, and
        a denture base inner surface comprising a fitting surface having a size and shape to engage the wearer's upper or lower jaw;
    b. a lid that fits over the denture base inner surface comprising a lid inner surface having a structure that comprises a replica of at least a portion of the wearer's edentulous ridge, wherein the replica aligns within the denture base inner surface when the lid and denture base are assembled; and
    c. a cavity between the lid inner surface and the denture base inner surface when the lid and the denture base are assembled;
        wherein the lid comprises an introduction port having an opening that extends from a lid outer surface into the cavity.

2. The apparatus of claim 1, further comprising a seal between the denture base and the lid around a perimeter of the apparatus when assembled.

3. The apparatus of claim 1, wherein the replica comprises a replica of a coronal portion of anterior and posterior dentition.

4. The apparatus of claim 1, wherein the structure on the lid inner surface further comprises a replica of the wearer's soft palate.

5. The apparatus of claim 1, wherein the denture base is comprised of polymeric material that has a Shore D hardness value between 40 and 100 when cured.

6. The apparatus of claim 1, wherein the denture base is a full-arch denture base that covers a full edentulous ridge of the wearer.

7. The apparatus of claim 1, wherein the denture base inner surface is comprised of a first material comprising a polymer composition that comprises reactive groups; and the apparatus further comprises a polymerizable soft liner material within the cavity comprising a second material adjacent the tray inner surface comprising reactive groups adjacent reactive groups of the denture base inner surface.

8. The apparatus of claim 7, wherein the soft liner material is between the replica of the lid and the inner surface of the denture base.

9. The apparatus of claim 1, wherein the denture base further includes denture teeth secured to the denture base outer surface.

10. A method of making a denture device for a wearer having an edentulous ridge, comprising
   a. obtaining a denture base having an outer surface, an inner surface and a fitting surface;
   b. obtaining a lid having a structure comprising a replica of at least a portion of the wearer's edentulous ridge;
   c. assembling the denture base and the lid by aligning the replica of the lid within the fitting surface of the denture base to form a cavity;
   d. providing a curable soft liner material within the cavity between the replica of the lid and the fitting surface by injecting the curable soft liner material into the cavity through an introduction port in the lid; and
   e. curing the curable soft liner material to form a soft liner within the cavity.

11. The method of claim 10, further comprising bonding a lower surface of the soft liner to the inner surface of the denture base.

12. The method of claim 10, wherein the inner surface of the denture base comprises a polymeric material having reactive groups, and the method comprises chemically bonding the inner surface with the curable soft liner material during the curing step.

13. The method of claim 10, comprising forming an impression of the replica in the soft liner.

14. The method of claim 10, further comprising forming the lid and the denture base through an additive manufacturing process.

15. The method of claim 10, comprising forming the lid and the denture base by a three-dimensional printing process, and forming the soft liner by introducing the curable soft liner material into the cavity by an injection molding process.

16. The method of claim 10, further comprising securing denture teeth to the outer surface of the denture base.

* * * * *